United States Patent [19]

Harris

[11] Patent Number: 4,514,865
[45] Date of Patent: * May 7, 1985

[54] STEMMED FEMORAL COMPONENT FOR THE HUMAN HIP

[76] Inventor: William H. Harris, 665 Concord Ave., Belmont, Mass. 02178

[*] Notice: The portion of the term of this patent subsequent to Sep. 27, 2000 has been disclaimed.

[21] Appl. No.: 506,103

[22] Filed: Jun. 20, 1983

Related U.S. Application Data

[63] Continuation-in-part of Ser. No. 369,510, Apr. 19, 1982, Pat. No. 4,406,023.

[51] Int. Cl.³ ............................................... A61F 1/04
[52] U.S. Cl. ...................................... 3/1.913; 3/1.91; 128/92 C; 128/92 CA
[58] Field of Search ................... 3/1, 1.9, 1.91, 1.911, 3/1.912, 1.913; 128/92 C, 92 CA

[56] References Cited

U.S. PATENT DOCUMENTS 4,406,023 4/1982 Harris .................................. 3/1.913

Primary Examiner—Richard J. Apley
Assistant Examiner—David J. Isabella
Attorney, Agent, or Firm—Wolf, Greenfield & Sacks

[57] ABSTRACT

A stemmed femoral component for the human hip for which fixation is provided in one embodiment by bony ingrowth and which may be easily removed for replacement thereof by an osteotone. The two-piece component includes a stem which is elongated and has on its proximal end a Morse cone and a laterally extending collar adapted to reside on the cortical bone in the region of the femoral neck. In the one embodiment the stem is textured or provided with a porous material on its outer surfaces only in the metaphyseal portion and only on the anterior, lateral, and posterior surfaces. The medial surface is smooth, as is the diaphyseal portion of the stem. In this manner, bony ingrowth takes place only in regions that can be reached with a osteotone for removal. A threaded extractor and mating hole in a driving platform may also be provided for removal. In a second embodiment a cement such as methylmethacrylate is used in place of the bony ingrowth on the anterior, lateral and posterior surfaces of the metaphyseal portion of the stem.

11 Claims, 7 Drawing Figures

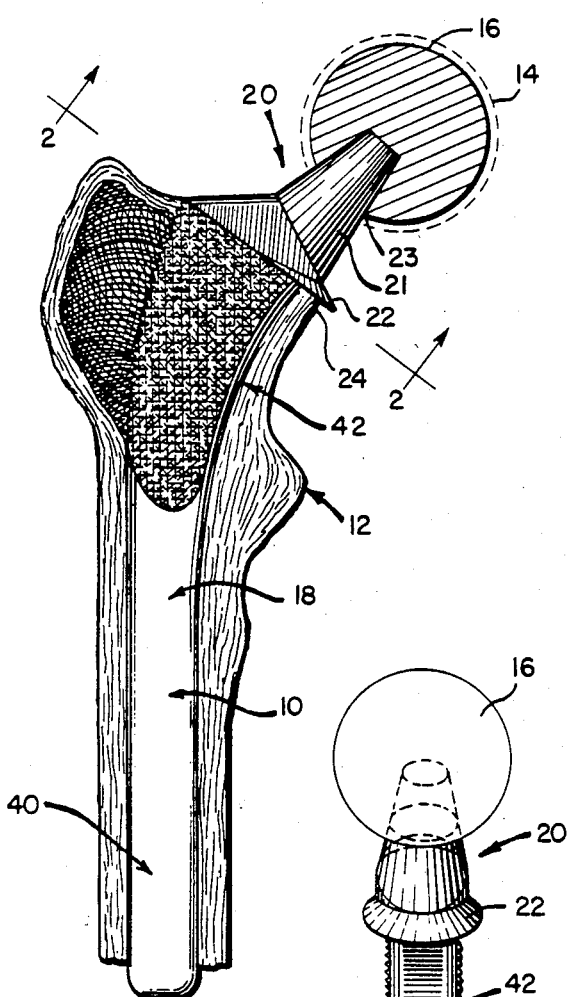
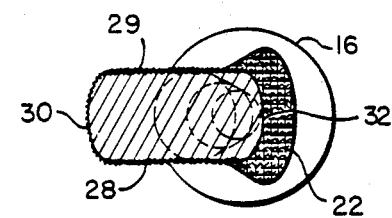
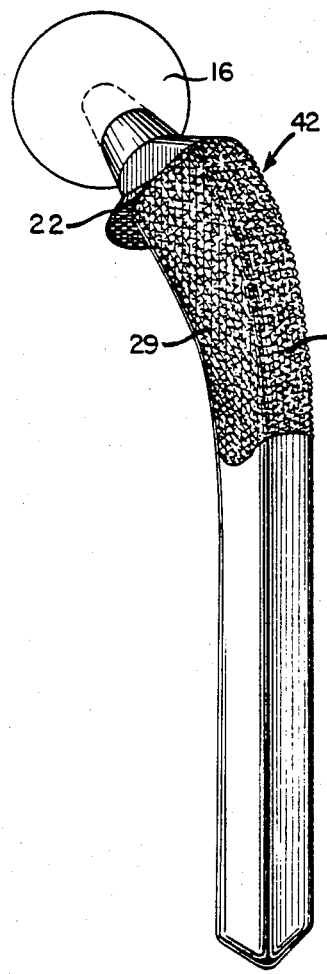
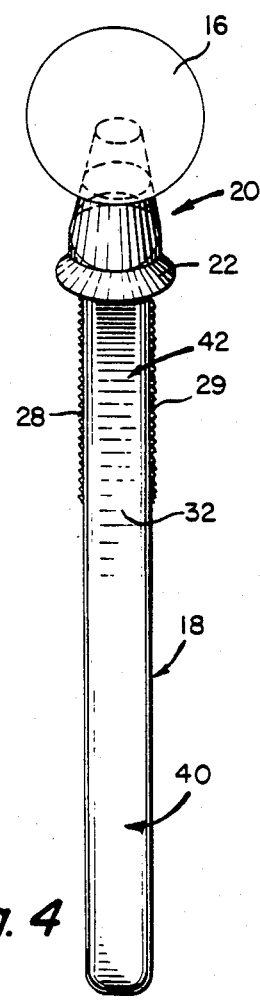
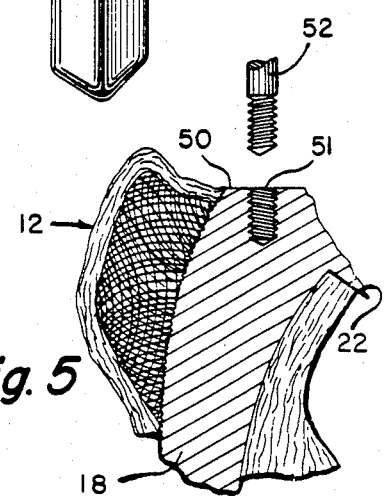

STEMMED FEMORAL COMPONENT FOR THE HUMAN HIP

This application is a continuation-in-part of my copending application Ser. No. 06/369,510 filed Apr. 19, 1982 now U.S. Pat. No. 4,406,023 entitled "Stemmed Femoral Component For The Human Hip".

FIELD OF THE INVENTION

This invention relates generally to prostheses and more particularly to femoral components of artificial human hip joints.

BACKGROUND OF THE INVENTION

Load-carrying skeletal members, such as the human hip, frequently are rendered non-functional because of fracture, damage, disease, resections for malignancy or disease, or because of pain or malformation. Such members are commonly repaired by total joint replacement with artificial components, and one type of bone replacement that has been particularly successful over the past 22 years is that of the human hip. Such hip prostheses typically include a femoral portion or component which is implanted in the femur and an acetabular component which is secured to the pelvis. The femoral component includes a head which rotates in a socket formed in the acetabular component. Examples of such prostheses are illustrated in U.S. Pat. Nos. 3,744,061; 4,012,796; 4,146,936; 4,156,943; 3,808,606; 3,102,536; and 4,080,666.

Many of these known prosthetic devices require the use of cement for embedment of the femoral component into the hollow bone structure. While many known cemented systems usually provide uniform distribution of mechanical loads, elimination of relative motion between the prostheses and the bone, and satisfactory load-per-unit area, many are also subject to problems associated with the toxicity of the cement, necrosis of the adjacent bone and incomplete filling of the cavity in the bone, and absence of resiliency. In addition, various reports of long-term results of cemented total hip replacements with a minimum follow-up of ten years show that the loosening rate on the femoral side is in the neighborhood of 30 to 50 percent. Specifically, Moreland (Moreland, J. R.; Gruen, T. A.; Mai, L.; and Amstutz, H. C.: "Aseptic Loosening of Total Hip Replacement: Incidence and Significance," *In the Hip: Proceedings of the Eighth Open Scientific Meeting of The Hip Society*, pp. 281–291, St. Louis, C. V. Mosby, 1980) reports a 44 percent loosening rate on the femoral side for periods of less than ten years; Salvatti, et al. (Salvatti E. A.; Wilson, P. D., Jr.; Jolley, M. N.; Vakili, F.; Agialli, P.; and Brown, G. C.: "A Ten Year Follow-up Study of Our First One Hundred Consecutive Charnley Total Hip Replacements", 63A *J. Bone Joint Surg.*, 753–767, 1981.) indicates that the femoral components were loose in 33 percent of the cases studied; Mueller (Mueller, M. E. "Long Term Follow-up of Total Hip Replacements" presented at the AOA International Symposium on "Frontiers in Total Hip Replacement", May 1981, Boston Mass.) reports that loosening caused a reoperation rate of about 20 percent in ten years; and a Mayo Clinic report (Coventry, M. B.: "Ten Year Follow-up Study of Total Hip Replacement at the Mayo Clinic", presented at the AOA International Symposium on "Frontiers in Total Hip Replacement," Boston, Mass., May, 1981) indicates a 30 percent rate of failure in the fixation of the femoral component within ten years. Methylmethacrylate is used as a cement in many such implants, and it has been shown that a membrane with synovium-like characteristics forms at the junction of the cement and the bone as a biological response to methylmethacrylate. (Goldring, S.; Schiller, A.; and Harris, W. H.: "Synovial Like Transformation at the Cement Bone Interface Following Total Hip Replacement", presented at the AOA International Symposium on "Frontiers in Total Hip Replacement," May 1981, Boston. Mass.) This membrane is characterized by the enhanced capacity to generate prostaglandin $E_2$ (PG E2) and collagenase, two of the key ingredients for bone destruction.

Because of the problems associated with earlier cemented implants, more recent developments in orthopedic research have been directed at generating implants which are fixed to the skeleton by bony ingrowth without the use of any cement. Examples of devices utilizing the bony ingrowth technique are illustrated in U.S. Pat. Nos. 3,314,420; 2,688,139; 3,808,606; and 3,938,198. Two major types of such implants are femoral surface replacements and intramedullary, stemmed femoral components. Experience has shown that the use of surface replacements on the femoral side for total hip replacement is not particularly successful. Failure rates of 27 percent and 39 percent have been reported by Capello (Capello, W.: "Results of Synovium Surface Replacement", presented at the AOA International Symposiumm on "Frontiers in Total Hip Replacement", May 1981, Boston, Mass.) and Freeman (Freeman, M. A. R. "Results of I.C.L.H. Surface Replacement", presented at the AOA International Symposium on "Frontiers in Total Hip Replacement", May 1981, Boston, Mass.) with follow-up periods of about three years. The reasons for this high failure rate include osteoporosis from disuse, bone resorption from peak stresses, femoral neck fracture, lysis, avascular necrosis, and technical errors, and in certain patients with severe disease, the lack of sufficient bone stock. As a result stemmed implants are generally considered to be most desirable, and the majority of the devices used, are stemmed components. Although some of the above stemmed implants are satisfactory for most purposes, none of them employing bony ingrowth fixation allows for easy removal of the implant should that become necessary because of metal fatigue, or other problems.

SUMMARY OF THE INVENTION

This invention relates generally to a prosthetic device for the human hip and more particularly to the femoral component thereof which in one embodiment utilizes bony ingrowth for attachment and which is configured for easy removal, if necessary. The femoral component of this invention is made of metal and comprises two pieces, a head and an elongated stem. The stem includes an upper, metaphyseal portion which has a roughly trapezoidal shape and a generally rectangular cross-section for rotational control, and a lower diaphyseal portion which has a generally circular cross-sections which is contiguous with the metaphyseal portion. The diaphyseal portion is adapted to extend into the diaphyseal or isthmus area of the medullary canal of the femur. Secured to the upper, proximal end of the stem is a medially extending collar, and disposed on the collar is a Morse cone femoral neck which is continuous with the collar. The collar is adapted to rest on the cortical bone in the region of the femoral neck, and the collar is contiguous with the metaphyseal portion of the stem and rests on the calcar area of the proximal end of the femur.

In accordance with one embodiment, the exterior surfaces of three sides of the metaphyseal portion of the stem are textured or are provided with a porous material which permits bony ingrowth for securing of the implant. This porous material is disposed only on the anterior, lateral, and posterior surface of the metaphyseal portion. The medial surface of the metphyseal portion and the entire diaphyseal portion are smooth, permitting no bony ingrowth in those areas. The collar extends laterally beyond the exterior surfaces of the stem only adjacent the smooth medial surface, so that all of the areas in which bony ingrowth is permitted to occur can be reached with an osteotone, and the entire stem can be easily removed if necessary. A threaded hole may be provided in a driving platform of the stem for use in conjunction with a similarly threaded extractor to facilitate removal of the stem.

In accordance with a second embodiment of this invention, a precoating of cement is used rather than bony ingrowth on the anterior, lateral and posterior surfaces of the metaphyseal portion to achieve fixation. The prosthetic device in other respects is the same as that in the first embodiment. The physical arrangement of the parts is such that it makes much easier the removal of the prosthetic device whether fixation be achieved by bony ingrowth, cement or some other technique.

This invention overcomes the deficiencies of many of the prior art prosthesis by providing a stemmed implant which is easily removable by use of an osteotone, should that become necessary. In addition, the stemmed femoral component of this invention permits rapid bony ingrowth, reduces stress on the stem, reduces stress on the stem-bone interface medially, reduces disuse osteoporosis and provides for rotational control.

BRIEF DESCRIPTION OF THE DRAWING

The objects, advantages, and features of this invention will be more clearly appreciated from the following detailed description taken in conjunction with the accompanying drawing in which:

FIG. 1 is a partially cut-away pictorial view of the femoral component of one embodiment of this invention implanted in a femur;

FIG. 2 is a cross-sectional view of the component taken on section 2—2 of FIG. 1;

FIG. 3 is a perspective view of the anterior and lateral surfaces of the component of FIG. 1;

FIG. 4 is a view of the medial surface of the component of FIG. 1;

FIG. 5 is a partially cutaway view of an alternative embodiment of the implant of FIG. 1 showing an extractor;

DETAILED DESCRIPTION OF THE PREFERRED EMBODIMENT

Figure 6:
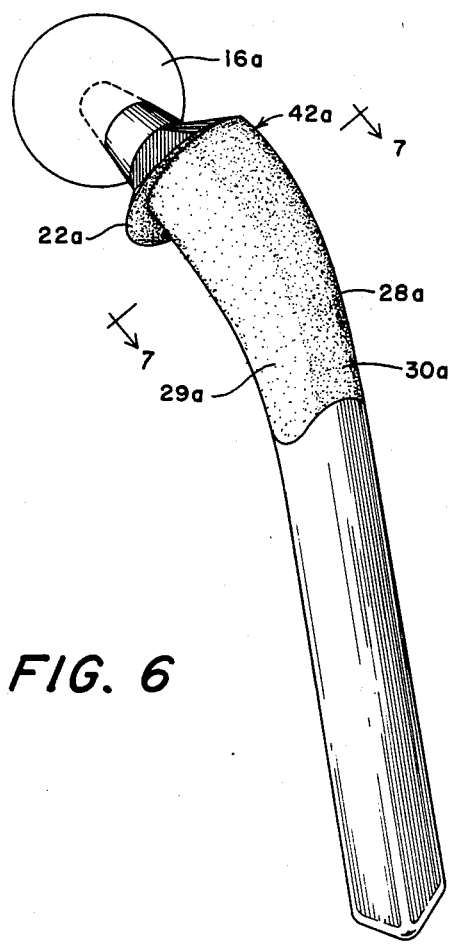
FIG. 6 is a view similar to FIG. 3 of a second embodiment of this invention.

With reference now to the drawing and more particularly to FIG. 1 thereof, a femoral component 10 of this invention is shown implanted in femur 12, its natural head 14 suggested by broken lines having been removed prior to insertion of the femoral component. Component 10 includes a femoral head 16 and a femoral stem 18 which is adapted to be inserted into the medullary canal of femur 12. The stem includes a large, flat, laterally extending collar 22, an upper, metaphyseal portion 42 and a lower diaphyseal portion 40. Collar 22 is adapted to rest on the cortical bone 24 in the region of the natural femoral neck, is contiguous with metaphyseal portion 42 which occupies a major portion of the metaphyseal area of the proximal end of the femur. Metaphyseal portion 42 is contiguous with diaphyseal portion 40 and has a rectangular cross-sectional shape, including a medial surface 32, a lateral surface 30, a posterior surface 29, and an anterior surface 28, each surface being adapted to face a corresponding side of femur 12. The metaphyseal portion 42 of the stem is adapted to be positioned in the medullary area of the femur 12, while the diaphyseal portion 40 is adapted to extend into the isthmus of the medullary canal of the femur 12 and has a rounded cross-sectional configuration to conform to the shape thereof.

Lateral surface 30, posterior surface 29 and anterior surface 28 are each either textured or provided with a porous material to produce a porous surface for permitting bony ingrowth to cause fixation of the implant. Collar 22 extends laterally beyond the stem 18 only adjacent the medial surface 32 and has a similar porous surface on its underside for permitting bony ingrowth. Medial surface 32 and the entire diaphyseal portion 40 are smooth and permit no bony ingrowth.

Typically, the head 16 is coupled to stem 18 by a Morse cone femoral neck 20 connected to collar 22. Morse cone 20 is provided with angular surfaces 21, and femoral head 16 is provided with a mating opening 23. When head 16 is inserted onto the cone 20, a very firm friction fit is formed, and no additional fasteners are required. Head 16 may be readily removed by proper twisting and pulling in the event that it needs to be changed or replaced for any reason after implantation or after bony ingrowth has occurred. This can be done without disturbing the bony ingrowth which provides femoral stem fixation. Experience has shown that in the revision of conventional total hip replacements, it is not uncommon to require a change in the femoral component.

In constructing a stemmed implant utilizing bony ingrowth, it has been found that there are several requirements which must be considered. In particular, the implant must be provided with rigid immediate fixation so that the bone can properly grow into the porous surface of the implant. If motion occurs prior to fixation, fibrous tissue will grow instead of bone. A second requirement is excellent apposition. Typically, a gap of one millimeter or two millimeters will exceed the growth capacity of the bone and will not result in bony ingrowth. Thus, wide-spread and accurate apposition is absolutely essential. Thirdly, it is desirable that the bony ingrowth provide fixation predominantly in areas other than at the lower or distal end of the stem. If bony ingrowth provides fixation at the distal end of the stem and not at the upper or proximal end, two major problems may result. The first is a substantial stress shielding of the bone immediately adjacent to the fixation area which has a high probability of leading to major bone loss. The second problem relates to the inherent fatigue of the metal. If the stem is rigidly fixed to the bone at the distal end only and is not rigidly supported at the proximal end adjacent the femoral neck, there is a high probability of fatigue fracture of the stem. Fourthly, in any such stemmed implant, some mechanism must be provided to allow for removal of the implant should that become necessary. It is particularly desirable to permit removal of the implant by use of an osteotone.

The present invention takes into consideration each of these requirements for a stemmed implant. Excellent apposition is provided by proper shaping of component 10 and by careful reaming of the femur. Fixation is insured in areas other than the distal end of the component by providing the exterior of stem 18 with a porous surface only in the metaphyseal portion 42 and only on lateral surface 30 and posterior surface 29 and anterior surface 28. The porous surface of the metaphyseal portion permits bony ingrowth and provides a bond between that portion of the bone only and the stem. The smooth surface of the diaphyseal portion 40 and of the medial surface 32 of the metaphyseal region prevents bony ingrowth and therefore prevents the forming of any bond between the bone and the stem in that area.

Rigid immediate fixation is provided by the rectangular shape of the metaphyseal portion of the stem and by the fit of the diaphyseal portion in the isthmus of the medullary canal. Since the metaphyseal portion of the prostheses has much wider anterior and posterior surfaces than lateral and medial surfaces, rotation of the stem within the femur is prevented after implantation. Also, the diaphyseal portion of the stem, is provided with a snug interference fit within the isthmus of the medullary canal which prevents any movement of the stem generally parallel to the direction of elongation of the femur. Since there is no need to have room for any sort of cement such as methylmethacrylate, and since there is no bony ingrowth layer, the diaphyseal portion of the stem can be very large and can occupy the full volume of the available space. If the medullary canal is not large enough it can be reamed so that the stem, with its large cross-section, can be fitted therein.

The mechanism which provides for easy removal of the stem will now be described. Collar 22 is flat and does not extend transversely of the metaphyseal portion 42 very far adjacent the lateral, posterior or anterior surfaces. Collar 22 is provided with a large transverse dimension only adjacent the medial surface which is not porous and has no bony ingrowth. Thus, access by an osteotone is permitted to all surfaces having bony ingrowth, the anterior, lateral, and posterior surfaces of the metaphyseal region for removal of the bony ingrowth. The areas to which no access is permitted, the medial surface and the entire disphyseal portion, have no bony ingrowth and need not be reached by an osteotone.

While a porous surface may also be provided on the underside of the collar adjacent cortical bone 24 for permitting bony ingrowth, this area may also be reached by an osteotone for its removal. Head 16 may be readily removed from Morse cone 20 to provide greater access by an osteotone to the surfaces having bony ingrowth.

Optionally, a driving platform 50 may be provided in stem 18 adjacent collar 22, and in the center of platform 50 a recess 51 is provided which is adapted to accept a threaded extractor 52 for removal of the femoral stem.

Should removal of component 10 become necessary, in the absence of loosening, it may be readily extracted by a direct use of an osteotone to cut the bony ingrowth and additionally by use of the optional screwed-in extractor. First, head 16 is removed, as described, to provide access to the stem by an osteotone. Then a direct osteotomy is performed on the anterior, lateral and posterior surfaces of the metaphyseal portion of the stem and to the underside of the collar. The femoral component may be withdrawn by securing a threaded extractor to collar 22 on driving platform 50 by means of threaded hole 51 and by pulling on the extractor.

The above-described femoral stemmed component provides numerous advantages over the prior art and renders the prostheses of this invention far superior to those presently being used. Since a porous surface is provided only in the metaphyseal portion 42 of stem 18 and on the underside of collar 22, bony ingrowth takes place in the region of the trabecular bone where bony ingrowth occurs most rapidly. Thus, the time necessary for immediate rigid fixation prior to the onset of bony ingrowth will be as short as possible. In addition, bony ingrowth takes place only in regions that can be reached with an osteotone should removal be necessary. The presence of bony ingrowth only in the metaphyseal region causes major stress transfers to occur only at the proximal end of the stem and not at the distal end or in the diaphyseal portion. This is important in maintaining a relatively normal stress environment for the metaphyseal region of the proximal part of the femur, and leads to minimal disuse osteoporosis. One particular advantage of providing bony ingrowth on the surfaces of the proximal part of stem 18 is that bony ingrowth in a three-dimensional porous material permits resistance against tension. Thus, not only is there support for the component provided on the medial side in compression, there is support provided on the lateral, anterior and posterior sides provided by the bony ingrowth for resisting tension. Additionally, since the diaphyseal region has no bony ingrowth, there are no high stress concentrations which can occur if bony ingrowth is present over that portion of the stem and not over adjacent portions, and which could cause a fatigue fracture at that site. In the only region where there is bony ingrowth, namely, the metaphyseal portion 42, there is a very large and very strong substrate, and fracture in this area is extemely unlikely. The large size of the diaphyseal portion of the stem also adds strength to the component.

Another novel advantage provided by the present invention is found in the configuration of the collar. Since the collar is flat and extends medially adjacent medial surface 32, it serves as a stop to prevent the stem from being forced downwardly into the femur. Thus, the collar provides resistance against the tendency for component 10 to be forced into varus. It also provides proximal stress transfer. The most dramatic area of decreased stress or stress shielding after insertion of a stemmed femoral component is in the calcar region. The bony ingrowth under the collar of the present invention improves fixation, increases resistance against varus displacement, and directly transfers stress on the prosthes's to the proximal medial cortical femoral bone. This feature reduces stress on the stem, reduces stress on the component-bone interface medially, and reduces disuse osteoporosis.

Typically, head 16, stem 18, and Morse cone 20 are formed of a metal such as a chrome-cobalt alloy such as Vitallium, a Trademark of Howmedica Inc, Rutherford, N.J. or a titanium aluminum-vanadium alloy such as Tivanium, a Trademark of Zimmer U.S.A. of Warsaw, Ind., although any other suitable material may be used.

Preferably, the pore size of each of the porous surfaces of the invention is above 150 microns but less than 1000 microns. If the surfaces are textured to produce the desired porosity, stem 18 is generally cast with the porous surfaces formed thereon. If a separate layer of material is used, this layer is typically formed of the same material as the stem and is sintered thereto. The separate layer may also be formed of a ceramic material which is affixed to the appropriate portions of the stem in a known manner.

While the embodiment described above and illustrated in FIGS. 1–5 stresses the use of bony ingrowth to achieve fixation, the configuration of the implant shown in those figures also provides substantial benefit in facilitating removal of the implant when fixation is accomplished by the use of cement. Among the most recent developments in cemented implants is the stemmed femoral component precoated with polymethylmethacrylate (PMMA), such as is disclosed in U.S. Pat. Nos. 4,280,233 and 4,281,420. When cemented implants are used and removal is necessary, the same problems exist with respect to their removal as exists in connection with implants fixed by bony ingrowth.

Figure 7:
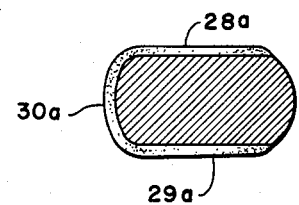
FIG. 7 is a cross-sectional view of the component of FIG. 6 taken on section 7—7 of FIG. 6.

In FIGS. 6 and 7 the implant illustrated is adapted to be cemented in the femur. The shape of the stem 18a, femoral head 16a and laterally extending collar 22 are essentially the same as in the embodiment of FIGS. 1–5, although the stem may be somewhat thinner than the first embodiment for reasons which are set forth below. The upper third of the anterior, lateral and posterior surfaces 29a, 30a and 28a of the metaphyseal portion of the stem 18a are precoated with a film of cement such as PMMA, while medial surface 32a is free of such a coating. A cement coating may also be provided under the collar 32a.

The component may be implanted by applying cement to the medullary canal of the femur during the implant operation, which then creates a cement to cement bond between the implant and bone. To make room for that application of cement, the stem of this embodiment is thinner than that of the first embodiment. Any bonding which occurs between the metal and bone solely because of the cement applied in the operating room is substantially weaker than the bond achieved by the contact of the precoated cement and cement applied in the operating room. The better bond is of course more difficult to break, and the configuration of the implant of this invention faciliates that action.

When the stem 18a is to be removed, an osteotomy is performed on the precoated surfaces, all of which are accessible because of the configuration of the collar 22a. The component may be removed by an extractor in the manner described in connection with FIG. 5 above.

Modifications and improvements will occur within the scope of this invention, and the above description is intended as exemplary only. The scope of this invention is defined by the following claims and their equivalents.

I claim:

1. A femoral component for a hip prosthesis for the human hip comprising:
   a femoral stem adapted to fit into the medullary canal of the femur, said femoral stem having an upper portion and a lower portion, said upper portion having lateral, medial, anterior and posterior surfaces;
   a collar formed on a proximal end of the stem adjacent the upper portion thereof and extending transversely of the direction of elongation of the stem, said collar extending transversely beyond only selected ones of said lateral, medial, anterior and posterior surfaces on the proximal end of the stem, and said collar not extending transversely beyond surfaces of said upper portion of said stem other than said selected ones of said lateral, medial, anterior and posterior surfaces; and
   means for bonding said femoral stem to the femur, said bonding means being provided only on said other surfaces of said upper portion of said stem, said selected ones of said lateral, medial, anterior and posterior surfaces and the outer surfaces of said lower portion of said stem being free of said bonding means.

2. A femoral component as recited in claim 1 further comprising:
   a removable femoral head secured to the proximal end of the stem adjacent the upper portion of said stem above said collar;
   a neck provided on said proximal end of said stem and a recess provided in said head for receiving said neck for removably supporting said head.

3. A femoral component as recited in claim 1 wherein said selected ones of said lateral, medial, anterior and posterior surfaces comprise said medial surface of said stem, and said others of said lateral, medial, anterior and posterior surfaces comprise said anterior, lateral and posterior surfaces of said stem.

4. A femoral component as recited in claim 1 wherein said bonding means are precoated with a cement film.

5. A femoral component for a hip prosthesis for the human hip comprising:
   an elongated femoral stem adapted to be inserted into a medullary canal of a femur bone of a human being, said femoral stem having a metaphyseal portion adapted to be placed in a medullary area of the femur and a diaphyseal portion adapted to extend to an isthmus of the medullary canal of the femur, the metaphyseal portion of the stem having lateral, medial, anterior and posterior surfaces;
   cement bonding regions disposed on the lateral, posterior and anterior surfaces of said metaphyseal portion of said stem for bonding the proximal end of the femur to said stem, the medial surface of the metaphyseal portion of the stem and all external surfaces of the diaphyseal portion of the stem being free of cement bonding regions; and
   a collar disposed on the proximal end of said stem adjacent said metaphyseal portion thereof and extending transversely of the direction of elongation of said stem beyond the medial surface but not beyond the lateral, posterior and anterior surfaces for enabling a direct osteotomy to be performed on the lateral, anterior and posterior surfaces of the metaphyseal portion of the stem.

6. A femoral component as recited in claim 5 wherein said collar comprises cement bonding regions disposed on an undersurface thereof adjacent the femur for bonding said collar to the femur.

7. A femoral component as recited in claim 5 wherein said metaphyseal portion has a generally rectangular cross-sectional shape.

8. A femoral component as recited in claim 1 wherein said bonding means comprise cement bonding regions.

9. A femoral component as recited in claim 5 wherein said diaphyseal portion has a generally circular cross-sectional shape.

10. A femoral component as recited in claim 5 further comprising threaded removal means disposed on said metaphyseal portion of said stem adjacent said collar adapted for attachment to extractor means for removal of said stem from the femur bone.

11. A femoral component as recited in claim 5 further comprising:
- a femoral neck disposed on the proximal end of said stem adjacent said collar; and
- a spherical femoral head removably secured to said neck.

* * * * *